United States Patent
Ansley et al.

(10) Patent No.: US 6,716,434 B1
(45) Date of Patent: Apr. 6, 2004

(54) COMPOSITION AND METHOD FOR IMMUNOSTIMULATION IN NON-MAMMALIAN VERTEBRATES

(76) Inventors: Daniel R. Ansley, 404 S. Maple St., Ottawa, KS (US) 66067; Kenneth O. Willeford, 215 B Helen Cir., Starkville, MS (US) 39759

(*) Notice: Subject to any disclaimer, the term of this patent is extended or adjusted under 35 U.S.C. 154(b) by 0 days.

(21) Appl. No.: 09/666,009

(22) Filed: Sep. 19, 2000

(51) Int. Cl.⁷ .............................................. A61K 39/39
(52) U.S. Cl. ...................... 424/278.1; 424/531; 514/2; 514/12; 514/21; 514/885; 530/830
(58) Field of Search ............................. 424/531, 278.1; 514/885, 2, 12, 21; 530/830

(56) References Cited

U.S. PATENT DOCUMENTS 4,702,908 A * 10/1987 Thorbecke et al. ........... 424/88
5,219,578 A *  6/1993 Ansley ........................ 424/531
5,464,816 A * 11/1995 Nagai et al. ................... 514/2

* cited by examiner

*Primary Examiner*—David Saunders
(74) *Attorney, Agent, or Firm*—Serle Ian Mosoff

(57) ABSTRACT

This invention relates to compositions utilized to modulate the immune system of non-mammalian vertebrates. More particularly, the present invention relates to the use of low molecular weight substantially immunoglobulin free fractions isolated from mammals to induce a stimulated immune response in non-mammalian vertebrates.

8 Claims, 4 Drawing Sheets

COMPOSITION AND METHOD FOR IMMUNOSTIMULATION IN NON-MAMMALIAN VERTEBRATES

BACKGROUND OF THE INVENTION

It has long been known that mammals, when confronted with bacterial or viral infections, exhibit efforts at self-healing which are initiated by a complex physiological network referred to as the immune system. The immune system operates in response to a challenge to the mammal by initially recognizing the presence of a foreign organism or pathogen within the animal's body. In mammals, this is followed by an attack on the foreign organism by the neutrophils, macrophages and other "killer" cells of the immune system. This immune response functions or is "turned on" by a variety of immune system regulators which activate the various aspects of the immune system depending upon the type of insult confronting the subject animal.

A substantial component of the immune system is a group of structurally related glycoproteins, collectively known as immunoglobulins, contained within blood and extra cellular fluids. Five immunoglobulin classes have been identified: immunoglobulin G (IgG), IgM, IgA, IgD and IgE. The basic structural unit of each immunoglobulin class consists of two pairs of polypeptide chains joined by disulfide bonds. The five classes of immunoglobulins have different biological properties and different distributions in the body. The structure responsible for the biological properties of each immunoglobulin class is located on that part of the immunoglobulin molecule which is unique for each class-the Fc fragment. While some antibodies are produced at all times in normal animals, other antibodies are produced only in response to specific antigenic stimulation (e.g., when pathogenically challenged).

IgG is the major antibody class in normal mammalian systems and forms about 70% of the total immunoglobulin. IgG is evenly distributed between intra- and extra vascular pools. It is the first major antibody of the secondary immune response and belongs to the exclusive antitoxin class. IgG is a monomeric protein which can be divided into four sub-chains—two heavy chains "H" and two light chains "L". Taking the four sub-chains together each IgG molecule consists of one $H_2L_2$ unit with a molecular weight of proximately 140,000 Daltons. Molecules of the IgG class are actively transported across the placenta and provide passive immunity to newborns at a time when the infant's immune mechanisms are not developed.

The remaining four immunoglobulin classes are more narrow components of the immune system.

IgM is the first immunoglobulin class produced by the maturing fetus. IgM does not normally cross the placenta from the mother to fetus, but may be produced actively by the fetus prior to birth, especially if the fetus has been exposed to antigens by infection. IgA is found in relatively small amounts in serum and tissue fluids, but is present in high concentrations in external secretion such as saliva, tears, and bronchial secretions. IgE is also present in very low concentrations and appears to be associated with the histamine response. The last immunoglobulin class, IgD, is present in very low concentrations in secretions. IgD stimulates immature lymphocytes to multiply and differentiate thereby causing the production and secretion of other antibodies. Therefore, all immunoglobulin classes are important in immune system responses.

Modulation of the immune system to effect greater response to foreign agents has been an area of interest for some years. The development of specific antibodies through vaccination has long been utilized to provide mammals with long term immune defense mechanisms to specific microorganism forms.

Ansley, U.S. Pat. No. 5,219,578,Jun. 15, 1993 discloses a non-adjuvanted IgG containing caprine serum fraction. This fraction is useful as an immunostimulant in mammals when challenged by specified diseases.

Recent efforts in immunology have been directed towards the utilization of immune system regulating molecules, rather than one of the five classes of immunoglobulins, to provide increased immune system activity. It is believed that, through the use of immune regulating or immune modulating molecules, a state of general immune system hyperactivity can be induced which may help combat challenges to the immune system (e.g., pathogenic infection). Infection may arise from a wound site or may arise from an opportunistic blooming when the host organism is simply deprived of sufficient sleep. It is believed that an induced state of general immune hyperactivity would result in a therapeutic response to the challenge. This might be viewed as the opposite of the vaccination type response that produces a specific long-term immunity. If such a non-specific immune response could be initiated at will it could be utilized to either act alone or in conjunction with a conventional treatment directed towards the etiological agents, Such a mechanism could be based upon activation of phagocytic cells that are capable of responding to a wide range of infectious agents. It may also be that the T-lymphocytes, which are major mediators of the overall immune response, may act to enhance the operation of non-specific cellular immunity even though the T-lymphocytes themselves are a part of the specific immune response.

The search for agents which potentiate the immune response is a driving force in drug research. Cytokines and cationic peptides are two classes of "relativel" low molecular weight compounds which have shown promise in this area of research. At least nine immuno-defense peptide products are commercially available with annual sales of over $4 billion (Latham, P. W., 1999, Therapeutic peptides revisited *Nature Biotechnology* 17:755–757).

Bio-active peptides (such as "cationic peptides") are emerging as promising alternatives for combating antibiotic-resistant bacteria with minimum inhibitory concentrations reported from 1–100 µg/ml (Martin, E., T. Ganz, and R. I. lehrer, 1995. Defensins and other endogenous peptide antibiotics of vertebrates, *J. Leukoc. Biol,* 58:128–136; Hancock, R. E. W., 1997, Peptide antibiotics, *Lancet,* 349:418–422). Cationic peptides range from 16–18 amino acid residues for the protegrins (Ganz, T., and R. Lehrer, 1998. Antimicrobial peptides of vertebrates, *Curr. Opin. Immunol.,* 10:41–44.) to 29–35 residues for mammalian defensins (Sawa, T., and K. Turahashi, 1999, Antimicrobial peptides/proteins—application to the therapy of sepsis (article in Japanese), Masui, 48:1186–1193.). Due to a compositional prominence of lysine and arginine, they possess a net positive charge of at least 2, and usually 4, 5, or 6 (Hancock, R. E. W., 1997, Peptide antibiotics *Lancet,* 349:418–422).

Interleukin-1 (IL-1), tumor necrosis factor-α (TNF-α) and interferon (IFN) are three cytokines which participate in the immune response. IL-1 is involved in the host's response to antigenic challenge and tissue injury, and has been shown to increase the resistance of mice to pathogenic organisms such as Listeria, *Escherichia coli*, and *Candida albicans*

(Czuprynski, C. J., and Brown, J. F., 1987, Recombinant murine interleukin-1α enhancement of nonspecific antibacterial resistance, *Infection and Immunity* 55:2061–2065; Cross, A. S., Sadoff, J. C., Kelly, N, Bernton, F., and Genski, P., 1989, Pretreatment with recombinant murine tumor necrosis factor α/cachectin and murine interleukin 1α protects mice from lethal bacterial infection *The Journal of Experiment Medicine* 169:2021–2027; Pecyk, R. A., Fraser-Smith, E. B., and Matthews, T. R., 1989, Efficacy of interleukin-1β against systemic *Candida albicans* in normal and immunosuppressed mice, *Infection and Immunity* 57:3257–3258.). TNF-α and γ-IFN were able to increase the resistance of mice to *Salmonella typhimurium* (Morrissey, P. J., and Charrier, K, 1994, Treatment of mice with IL-1 before infection with increases resistance to a lethal challenge with *Salmonella typhimurium, The journal of Immunolgy* 153:212–219). Human α IFN's have potent antiviral and antiproliferative activities, and are currently being utilized as anticancer or antiviral therapeutic agents (Chang, C. J., Chen, T. T., Cox, B. W., Dawes, G. N., Stemmer, W., Punnonen, J., and Patten, P. A., 1999, Evolution of a cytokine using DNA family shuffling *Nature Biotechnology* 17:793–797).

Cationic peptides help defend against the constant assault of moderate numbers of bacteria. Each natural peptide has a broad but incomplete spectrum of activity. The host compensates for this by producing an array of different peptides that together have a broader spectrum of activity, and often work in synergy with one another. A single individual may produce dozens of different peptides and more than 500 natural cationic peptides have been discovered (Hancock, R. E. W., 1999. Host defence (cationic) peptides, *Drugs* 57:469–473).

Bio-active peptides have been found to possess antiviral, antibacterial, antifungal, and wound healing properties (Sanglier, J., Haag, Huck, T., and Fehr, T. 1993. Novel bioactive components from Actinomycetes. A short review (1988–1992), Res. Microbiol. 144:633–642; Mizuno, T., Wang G., Zhang J., Kawagishi H., Nishitoba, T., and Li, J, 1995; Reishi, *Ganoderma Lucidum* and *Ganoderma T sugea*. Bioactive substances and medicinal effects, *Food Rev. Int.* 11:151–166; Hancock, R E. W., 199, Host defence (cationic) peptides Drugs 57:469–473). A decameric pepide has even been shown to impede the growth and spread of established tumors (Folkman, J., 1999, Angiogenic zip code, *Nature Biotechnology* 17:749). It is believed that these "defense" peptides are more general in action than antibodies, and as such, have a broader range of activity (Hancock, 1999). These peptides have low toxicity to most mammalian cells and are therefore candidate for development as therapeutic agents (Maloy, W. L., and U. P. Kari, 1995. Structure-activity studies on magainins and other host defense peptides, *Biopolymers (Peptide Science)*, 37:105–122).

Industrially raised non-mammalian food animals such as chickens and turkeys are subjected to high stress and are more susceptible to disease than free range animals. It is common to provide such non-mammalian vertebrates with prophylactic amounts of various antibiotics and other disease preventative drugs to minimize disease related losses.

Non-mammalian species used as food animals are subjected to high stress levels during shipment to processing centers and while awaiting processing. Disease is common during such periods of stress.

More exotic animals, such as those kept in zoos, are subject to stress related and stress non-related diseases due to the artificial environments in which they live. A nonspecific immunostimulant would be desirable for both prophylactic and ameliorative purposes.

The cost associated with the administration of prophylactic agents and the inherent risk of residues of such drugs remaining in the edible portions of the food animal make it desirable to minimize the administration of such drugs. A simple and elegant means of accomplishing this is to increase the assertiveness of the non-mammalian vertebrate's own disease fighting systems.

Therefore, it is an object of the present invention to provide a means for modulating the immune response in non-mammalian vertebrates afflicted with disease.

Another object of the present invention is to provide a means for enhancing the ability of conventional antimicrobial medicaments by providing a concomitant stimulation of the animal's immune response.

Yet another object of the present invention is to provide a means of stimulating the immune response in non-mammalian vertebrates to heighten the animal's ability at self-healing when challenged by an infectious agent.

Yet another object of the present invention is to provide a means of prophylactically stimulating the immune response in non-mammalian vertebrates to heighten the animal's ability to avoid disease prior to being placed in a high stress environment.

The above and further objects and novel features of the invention will more fully appear from the following description and the examples contained therein.

SUMMARY OF THE INVENTION

Figure 1:
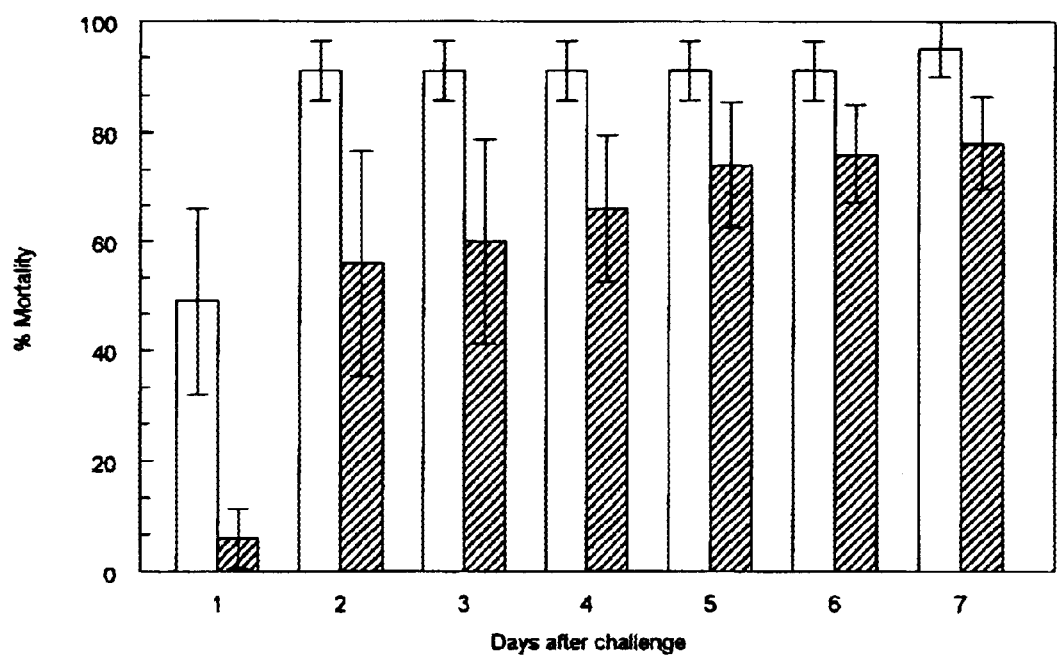
FIG. 1 represents the results obtained when chickens were injected with 30 cfu of *Pasteurlla multocida* on day 0 (open) and 5 mg of CSF-I2 on days −1 and 0 (hatched). Mortality was monitored daily for one week. Each bar represents the average mortality per cage (n=3) of 10 birds with its associated standard experimental error.
Figure 2:
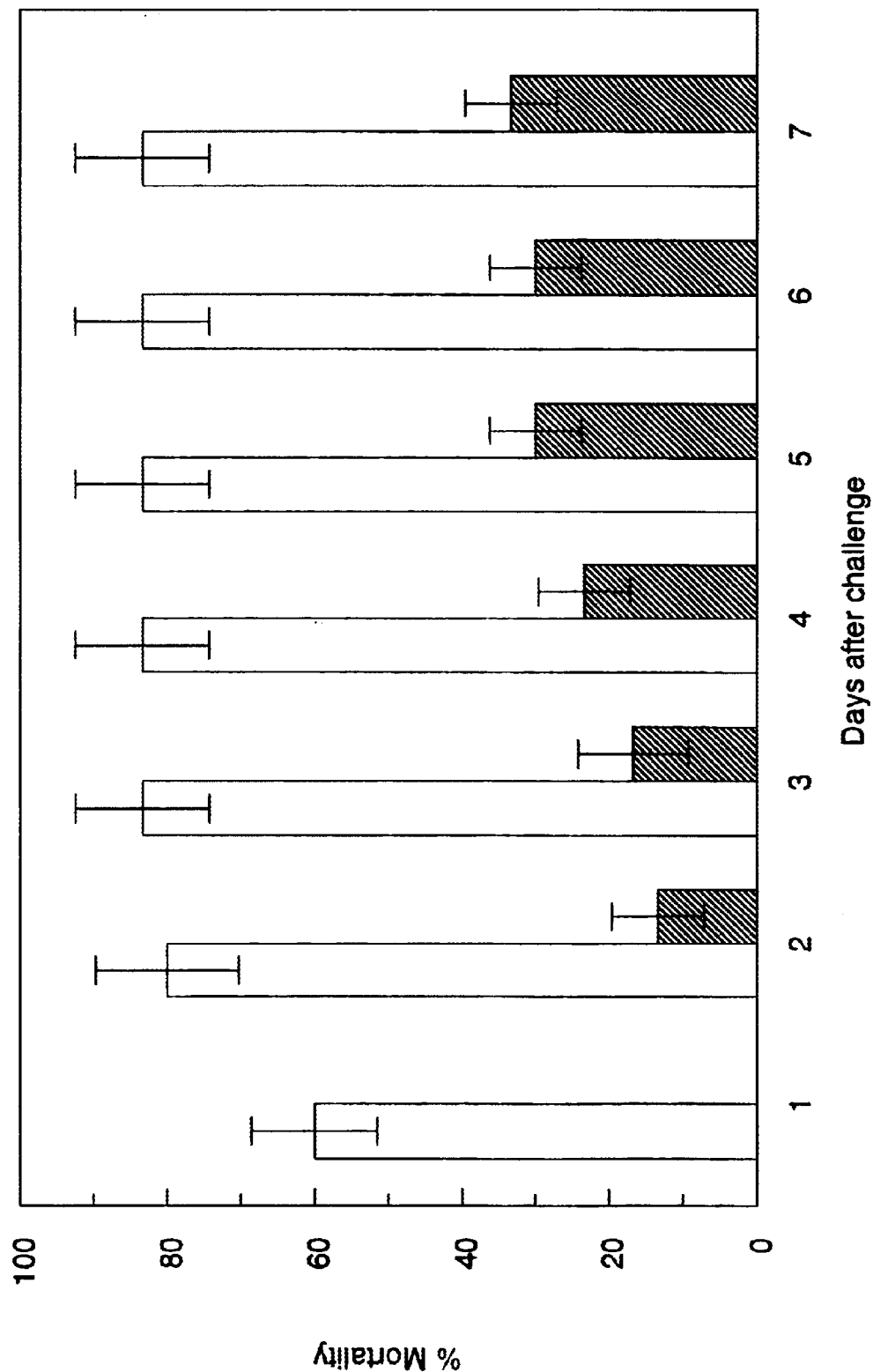
FIG. 2 represents the results obtained when chickens were injected with 18 cfu of *Pasteurella multocida* on day 0 (open) and 10 mg of CSF-I2 on days −1 and 0 (hatched). Mortality was monitored daily for one week Each bar represents the average mortality per cage (n=5) of 6 birds with its associated standard experimental error.
Figure 3:
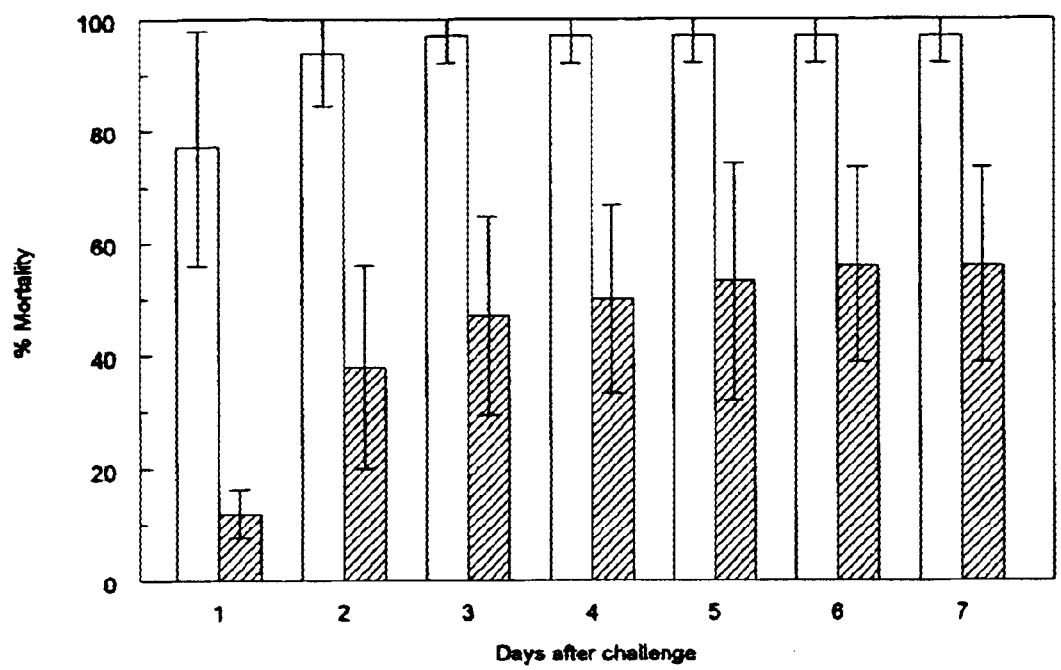
FIG. 3 represents the results obtained when chickens were injected with 28 cfu of *Pasteurella Multcida* on day 0 (open) and 10 mg of CSF-I2 on days −1, 0, and 1 (hatched). Mortality was monitored daily for one weeks Each bar represents the average mortality per cage (n=5) of 12 birds with its associated standard experimental error.
Figure 4:
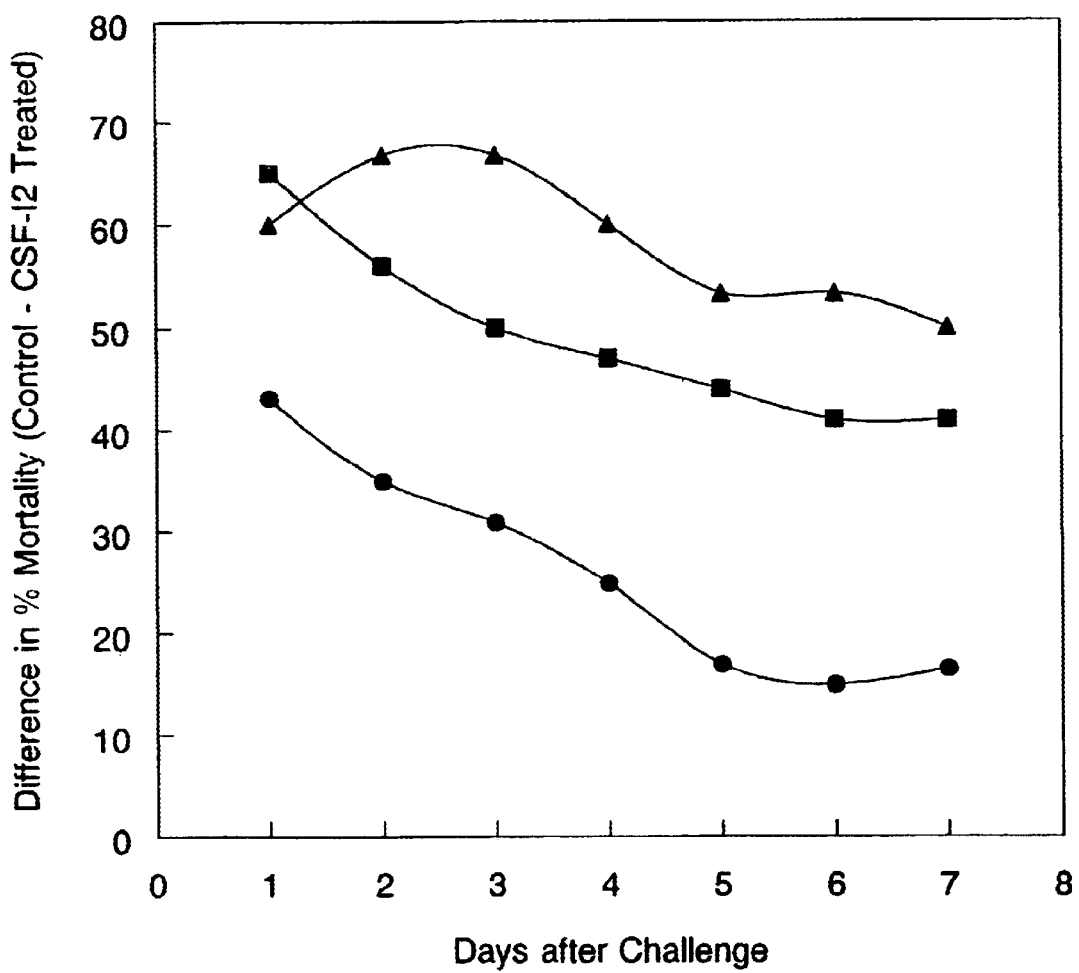
FIG. 4 represents the results obtained when the percent mortality of CSF-I2 treated chickens was subtracted from its associated control group's mortality for each treatment regime: 5 mg CSF-I2 (i.m., days −1 and 0), (●); 10 mg CSF-I2 (i.m., days 1 −and 0), (▲); and 10 mg CSF-I2 (i.m, days −1, 0, and 1), (■).

The present invention is broadly concerned with a unique method for cross species modulation of the immune system. Surprisingly, we have now determined that substantially immunoglobulin free material fractionated from mammalian serum referably goat serum, helps retard pathogenesis in non-mammalian vertebrate species.

The inventive method and inventive compounds derived thereby involve, generally, the isolation of a low molecular weight substantially immunoglobulin free fraction from the blood of a mammal. This mammal has not been pre-treated in any way nor have foreign antigens been artificially introduced to the mammal. The substantially immunoglobulin free fraction obtained from this mammal is then used to treat a non-mammalian vertebrate. The non-mammalian vertebrate can be any vertebrate species, such as birds, reptiles or fish.

Treatment of the non-mammalian vertebrate with the substantially immunoglobulin free fraction from the mammal stimulates the disease fighting systems of the non-mammalian vertebrate. The non-mammalian vertebrate is thereby assisted in overcoming the deleterious effects of a disease or malady.

DETAILED DESCRIPTION

We have now determined that material fractionated from mammalian serum, preferably goat serum, helps retard pathogenesis in non-mammalian vertebrates, supporting the belief that the substantially immunoglobulin free fraction is non-specific species independent.

Agents which retard pathogenesis may enable a host to mount a successful defense to challenges of the immune system. These agents can provide specific protection (i.e., in the form of antibodies) or be general in nature and enhance the overall immuno-response. Cytokines and cationic peptides are two such classes of non-specific defense agents.

The product of this invention is a non-adjuvanted stimulant of the animal's disease fighting systems. It is derived from mammalian serum and contains a mixture of serum proteins and peptides but is substantially free of immunoglobulins. Them mammalian species is preferably one from which relatively large quantities of blood may be drawn. It is convenient to use large animals to obtain greater quantities of serum. It is convenient to use domestic animals as they are readily available. Thus, convenient species are horses, cows, goats, sheep and pigs. Horses, cows and goats are preferred sources; goats are the most preferred serum source.

Albumin and immunoglobins (the two most abundant serum proteins) have molecular weights in the range of 66,000 to 155,000 daltons. The product of this invention is preferably produced utilizing a size fractionation procedure to remove proteins and other molecules having a molecular weight greater than 60,000 daltons, preferably greater than 25,000 daltons, most preferably greater than 8,000 daltons. Therefore, the product is substantially if not completely free of immunoglobin, albumin, and most cytokines.

The mammalian serum suitable for use in the invention is obtained from any convenient species of mammal. The collected serum is treated to separate it into high and low molecular weight fractions. A convenient cut-off point for the separation is in the range of 6000–8000 daltons although any cut-off point which effectively excludes immunoglobulins is acceptable. The primary requirement is that the fractionation remove substantially all immunoglobulins and albumin present from the low molecular weight fraction.

The serum may be fractioned by collecting the material which flows through a dialysis membrane possessing the desired molecular weight cut-off range. Spectra Por™ dialysis membranes with appropriate cut-off limits have been used successfully in preparing the products of this invention. Alternative fractionation procedures may also be used, provided that they remove serum fractions having a molecular weight cut-off of over 60,000 daltons, preferably over 25,000 daltons, most preferably over 8,000 daltons, and do not denature the peptides in the low molecular weight portion.

The low molecular weight material obtained from the fractionation process may be used immediately or it may be held for future use. If held for future use it is conveniently f lyophilized to a powder and stored at −70° C., until reconstituted with water for use. A typical fraction derived from goat serum has a proteinaceous content of 35%–40% based on an analysis of its nitrogen content.

The non-specific immunostimulant of this invention may be used to protect non-mammalian vertebrates against the onset of diseases or may be utilized to ameliorate the effect of diseases after they begin.

The immunomodulator provides useful protective properties in various genera of non-mammalian vertebrates. It can provide prophylactic or curative effects against such diseases as infection with Pasteurella in birds.

The treatment regime will vary with the animal and purpose of administration. Dosage amounts depend on the size of the animal being treated and range from a minimum of about 5 mg, preferably about 10 mg in avians. A second dose of the same size is typically administered between 1 and 3 days after the first dose.

The material may be administered alone, in conjunction with, at the same time as, or shortly before or after other treatments.

The material may be administered by any convenient route, such as intramuscularly, subcutaneously, intravenously or intraperitoneally. Topical administration, with a suitable adjuvant such as DMSO, is also effective against certain conditions. Oral administration is of particular usefulness for birds or other small or non-domesticated animals.

This low molecular weight material (hereafter referred to as CSF-I2) was subjected to testing to determine its ability to prevent the growth of bacteria. The results obtained show that the material is unable to inhibit growth of gram-negative or gram-positive bacteria.

The minimum inhibitory concentration (MIC) for a cationic peptide is usually in the range of 1 to 8 μg/mL (Hancock, R. E. W., 1997. Peptide antibiotics. *The Lancet,* 349:418–422). Two serotypes of Pasteurella showed no zone of growth inhibition when CSF-I2 was tested at 20 mg/l, over 2,500 times the upper MIC range recognized for cationic peptides, however, the product was able to inhibit Pasteurella pathogenesis in avian studies.

The material has been tested in non-mammalian vertebrates and has been determined to be effective in lessening or curing various diseases either when used alone or in conjunction with standard therapies. It has demonstrated effectiveness in avians against severe bacterial infection.

An animal model was established which permits the accurate assessment within a 2 day period of the immunoactivity present in CSF-I2, the material fractionated from caprine serum, against specific microbial challenges. Because the agent present in CSF-I2 significantly reduced specific-pathogen-free chicken mortality given a severe microbial challenge, it is possible that the immuno-active components may offer even a higher degree of protection against less virulent pathogenic challenges. The mechanism by which CSF-I2 precipitates its immuno-effect is unclear. Nevertheless, the evidence suggests that one possible route by which CSF-I2 sustains an immunocompetent status is by maintaining or increasing the CD4 population and reducing the CD8 cell population.

EXAMPLE

To determine the level of effectiveness of the low molecular weight compositions of this invention in ameliorating disease states in non-mammalian vertebrates, chickens were pathogenically challenged.

Specific-Pathogen-Free (SPF) layer chickens experience a severe rate of mortality when challenged by low doses (18 to 30 CFUs) of *P. multocida* X-73 (serotype 1). CSF-I2 was, however, able to significantly retard Pasteulla pathogenesis and promote higher survivability in SPF chickens. Three treatment regimes of CSF-I2 were examined in this study: 5 mg CSF-I2 (i.m., days −1 and 0), 10 mg CSF-I2 (i,m., days −1 and 0), and 10 mg CSF-I2 (i.m., days −1, 0, and 1), where day 0 represents the day of challenge. All treatments effectively reduced mortality through 1 week post-challenge. The 10 mg CSF-I2 dose regimes, however, clearly performed better than the 5 mg CSF-I2 dose regime. A statistical comparison between the two 10 mg CSF-I2 dose regimes was not made. However, there was no evidence that Day 1 administration of CSF-I2 improved survivability.

Animal Husbandry

Fertile eggs obtained from specific-pathogen-free (SPF) Leghorn chickens (HY-Vac Laboratory Eggs, Co., Adel, Iowa) were incubated under standard conditions. Ten hatched chickens were randomly assigned to each of 12 Horsfall-Bauer isolation units and raised until they were 5 weeks of age. Bird density was 360 $cm^2$ per bird at 5 weeks. All chickens had ad libitum access to feed and water. Birds were fed standard Mississippi State pullet starter diets. All diets met or exceeded National Research Council (1994) recommendations. The isolation room was a negative pressure environment maintained at 25° C. with a 12 hour light:12 hour dark cycle.

Bacteria

*Pasteurella multocida* X-73 (serotype 1) was obtained from the National Animal Disease Center, Ames, Iowa. *P. multocida* was grown in brain-heart infusion (BHI) broth (Dico Laboratories, Detroit, Mich.) at 370° C. After 16 hours incubation, 1 ml of culture was transferred to 100 ml of fresh BHI broth and incubated at 37° C. for 4 hours. The bacterial culture was serially diluted with sterile water in 10-fold increments. Each dilution was plated on blood agar plates and the colonies counted after 24 hours incubation to determine the number of colony forming units (CFUs) (Wang, C., and Glisson, J. R. 1994, Identification of common antigens of serotpe 1 and serotype 3 *Pasteurella multocida* in poultry expressed in vivo, *Avian Diseases* 38:334–340).

*Pasteurella multocida* P-1581*, Pasteurella multocida* ATCC 11039*, Psuedomonas aeruginosa* ATCC 27853*, Psuedomonas aeruginosa* PAO1*, Escherichia coli* ATCC 25922*, Enterobacter aerogenes, Enterbacter cloacae, Salmonea typhimurium, Staphylococcus aureus, Staphylococcus aureus* T-5706, and *Bacillus subtilis* were supplied from stock cultures by Dr. F. Champlin (Department of Biological Sciences, Mississippi State University) where they are maintained as reference organisms. Culture rehydration and cryoprotective maintenance conditions have been described previously (Darnell, K. R., Hart, M. E, and Champlin, F. R., 1987, Variability of cell surface hydrophobicity among *Pasteurella multocida* somatic serotype and *Actinobacillus ligniersii* strains, Journal of Clinical Microbiology 25:67–71).

Preparation of Caprine Serum Fraction (CSF-I2)

Goat serum was fractioned by collecting that material which flowed through a dialysis membrane (Spectra Por) possessing a molecular weight cut-off of 6–8,000 daltons. The low molecular weight material (CSF-I2) was lyophilized to a powder and stored at −70° C., until reconstituted with water for use. CSF-I2 was determined to be 37.5% proteinaceous based on its nitrogen content.

Bacterial Susceptibility Assays

Caprine serum and its high (over 8,000 daltons) and low molecular weight (less than 8,000 daltons) subfractions (each at a protein concentration of 20 mg/mL) were assessed for antimicrobial activity against both gram positive and gram negative bacteria by performing disk agar diffusion assays as described in Hart, M. E., and Champlin, F. R., 1988, Susceptibility to hydophobic molecules and phospholipid composition in *Pasteurella multocida* and *Actinobacillus lignieresii, Antimicrobial Agents and Chemotherapy* 32:1354–1359).

Antibiotic minimum inhibitory concentrations (MICs) were determined in Mueller-Hinton broth (Difco Laboratories, Detroit, Mich.) using the broth dilution method described previously (Damell, K. R., Hart, M. E., and Champlin, F. R., 1987, Variability of cell surface hydrophobicity among *Pastuerella multocida* somatic serotype and *Actinobacillus lignieresii* strains *Journal of Clinical Microbiology* 25:67–71).

Caprine serum and its dialysate containing immunoglobulins (over 8,000 daltons) were unable to inhibit bacterial growth. CSF-I2, material presumed to contain small molecular weight immunostimulatoty agents, also failed to inhibit the growth of all test bacteria, including two serotypes of Pasteurella (Table I).

TABLE 1

Susceptibility Of Selected Bacteria To Growth Inhibition By Caprine Serum Fractionated Into Its High (>8,000 Daltons) And Low (<8,000 Daltons) Molecular Weight Components.

| | [a]Zone of Inhibition | | | |
|---|---|---|---|---|
| | Low MW | | High MW | |
| Organism | 4 hr | 24 hr | 4 hr | 24 hr |
| Gram Negative Bacteria | | | | |
| *Pseudomonas aeruginosa* ATCC 27853 | 0 | 0 | 0 | 0 |
| *Pseudomonas aeruginosa* PAO1 | 0 | 0 | 0 | 0 |
| *Escherichia coli* ATCC 25922 | 0 | 0 | 0 | 0 |
| *Enterobacter aerogenes* | 0 | 0 | 0 | 0 |
| *Enterobacter cloacae* | 0 | 0 | 0 | 0 |
| *Salmonella typhimurium* | 0 | 0 | 0 | 0 |
| *Pasteurella multocida* ATCC 11039 | [b]IG | 0 | IG | 0 |
| *Pasteurella multocida* P-1581 | IG | 0 | IG | 0 |
| Gram Positive Bacteria | | | | |
| *Staphylococcus aureus* | 0 | 0 | 0 | 0 |
| *Staphylococcus aureus* T-5706 | 0 | 0 | 0 | 0 |
| *Bacillus subtilis* | IG | 0 | IG | 0 |

[a]MHA plates were streak inoculated with each of the assay organisms. Sterile filter paper disks impregnated with either the high or low MW caprine serum fraction were aseptically applied to the seeded plate surfaces. The plates were incubated for 24 h at 37° C., during which time inhibition of growth in areas surrounding the disks were visually assessed at 4 and 24 hr.

[b]IG, insufficient growth.

Bird Treatment

Two of 12 housing units were utilized as stress control pens. Birds assigned to these units did not receive a bacterial challenge or CSF-I2, but were sham handled in a manner consistent with all other birds. All inoculated birds received 18–30 colony forming units (CFUs) of *Pasteurella multocida* (X-73 strain, serotype 1) on Day 0. CSF-I2 and sham treatments, as well as bacterial challenges, were administered as 0.5 ml intramuscular injections.

Control birds housed in 5 of the remaining 10 units received Pasturella and sham treatment in a manner consistent with CSF-I2 treated birds. In experiment 1, treated birds were given 0.5 ml of a 10 mg/ml CSF-I2 solution (5 mg) on Days 1 −and 0. In the second experiment the treated birds received 0.5 ml of a 20 mg/ml CSF-I2 solution (10 mg) on Days −1 and 0. Treated birds in the third experiment received 0.5 ml of a 20 mg/ml CSF-I2 solution (10 mg) on Days −1, 0, and +1. The number of deaths were recorded and dead birds were removed from each unit at the same time each day. Each experiment utilized a 7 day trial period.

Flow Cytometry

Birds used in Experiment 3 were banded for identification. Five birds were selected at random from both the control and CSF-I2 treated populations. Two ml of blood was drawn from a wing vein and immediately processed for CD4 and CD8 counts. Blood was drawn 1 wk prior to the Pasteurella challenge in order to establish a representative baseline count. Blood was also collected on Day 1 in order to assess how the challenge and CSF-I2 treatment may alter these immunological parameters.

The CD4 and CD8 lymphocyte subset percentages in the peripheral blood were enumerated using a modification of a previously published method (Ainsworth, A. J., Dexiang, C., and Greenway, T., 1990, Characterization of monoclonal antibodies to channel catfish, *Ictalurus punctatus, Vet. Immunol. Immnopathol.* 26:81–92). Briefly, Ficoll-Paque isolated peripheral blood leukocytes were incubated with FITC-conjugated mouse anti-chicken CD4 or RPE-conjugated mouse anti-chicken CD8, or the appropriate isotype-matched control conjugates (Southern Biotechnology Associates, Inc., Birmingham, Ala.). Modifications to the procedure included a reduction of the incubation times to 5 minutes and analysis of samples using a FACSCalibur flow cytometer (Becton Dickinson, San Jose, Calif.).

Differential Cell Counts

A total of 200 nonerythroid, nonthrombocytic leukocytes were counted on duplicate blood smears stained with Wright's stain (Sigma Chemical Co., St. Louis, Mo.). The lymphocytes, heterophils, monocytes, eosinophils, and basophils were identified by the morphological characteristics described by Lucas, A. M., and Jamroz, C., *Atlas of avian hematology*, United States Department of Agriculture, Agriculture Monograph 25, Washington, D.C. 1961).

Statistical Analysis

All experimental protocols required a completely randomized design to be followed. Data demonstrating cumulative mortality and diagnostic blood parameters were analyzed by a one way analysis of variance and the means separated by Fisher's projected LSD procedure (SAS Package). A p value less than 0.05 had to be reached in order to be considered significant Results Birds receiving the 5 mg CSF-I2 treatment regime on Days −1 and 0 demonstrated significantly less mortality than inoculated controls throughout the study period (FIG. 1). However, the greatest difference was observed within the first 48 hours after challenge. During this 2 day period, the control group receiving 30 CFUs of *P. multocida* displayed the greatest mortality. Forty-nine percent of the control population were dead after 24 hours and 91% were dead by Day 2. The 5 mg CSF-I2 treatment regime, however, significantly retarded pathogenesis of the Pasted infection. Mortality in CSF-I2 treated birds were 6 and 56% on Days 1 and 2, respectively. Mortality gradually increased to 78% over the following 5 days of the study period.

Pathogenesis was retarded further when the CSF-I2 dose regime was doubled to 10 mg (FIG. 2).

A Pasteurella challenge of 18 CFUs caused rapid mortality in the control population (60% and 80% for Days 1 and 2, respectively). Mortality in the corresponding CSF-I2 treated group was only 0 and 13% on Days 1 and 2, respectively. Mortality on Day 7 had risen to 33%, which was significantly less than that of the control population (83%), and was less than that observed when the 5 mg CSF-I2 treatment regime was used.

The 10 mg CSF-I2 treatment regime was extended to include an additional delivery dose on Day 1 (after the daily observation). Twenty-eight CFUs of Pasteurella were used to initiate pathogenesis. After 24 h, mortality in the CSF-I2 treated population was significantly less than that of the control population (12% and 77%, respectively; FIG. 3). Mortality on Days 2 and 7 in CSF-I2 treated birds (38% and 56%, respectively) were consistently lower than that found in the corresponding untreated control population (94% and 97%, respectively).

Both treatment regimes utilizing 10 mg of CSF-I2 allowed birds to survive the bacterial challenge better than the 5 mg CSF-I2 treatment regime (FIG. 4). There was no evidence, however, which showed that the additional administration of CSF-I2 on Day 1 initiated a significantly better response than the 2 day dose regime of 10 mg CSF-I2.

The blood levels of CD4 and CD8 cells in unchallenged SPF chickens of Trial 3 were 18 and 26%, respectively. The microbial challenge caused the Day 1 CD4 cell count to decrease to 10%. Birds treated with CSF-12, however, expressed a CD4 cell count of 21%. There were no appreciable changes in CD8 levels due to CSF-I2 treatment. Differences cannot be considered significant at this time because the sample size (and the high death rate which made it impractical to follow the same birds) did not permit this determination.

I claim:

1. A method for the immunostimulation of a non-mammalian vertebrate, wherein a therapeutically effective amount of a composition of matter comprising the substantially immunoglobulin free, peptide containing portion of the blood of a mammal which passes through a dialysis membrane having a molecular weight cut-off of no greater than 60,000 daltons is administered to the non-mammalian vertebrate.

2. The method of claim 1 wherein the membrane has a molecular weight cut-off of no greater than 25,000 daltons.

3. The method of claim 1 wherein the membrane has a molecular weight cut-off of no greater than 8,000 daltons.

4. The method of claim 1 wherein the non-mammalian vertebrate is a reptile, fish, bird or amphibian.

5. The method of claim 1 wherein the non-mammalian vertebrate is a bird.

6. The method of claim 1 wherein the bird is a chicken or turkey.

7. The method of matter of claim 1 to stimulate the disease fighting systems of a bird against a challenge by *Pasteurella multocida* or *Samonella typhimurium.*

8. The method of claim 1 wherein the non-mammalian vertebrate is a fish.

* * * * *